(12) United States Patent
Langella et al.

(10) Patent No.: US 8,546,559 B2
(45) Date of Patent: *Oct. 1, 2013

(54) MODIFIED GALACTOMANNAN ETHERS

(75) Inventors: Valentina Langella, Milan (IT); Eva Baldaro, Milan (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 197 days.

This patent is subject to a terminal disclaimer.

(21) Appl. No.: 13/054,644

(22) PCT Filed: Jul. 14, 2009

(86) PCT No.: PCT/EP2009/058947
§ 371 (c)(1),
(2), (4) Date: Jan. 18, 2011

(87) PCT Pub. No.: WO2010/007040
PCT Pub. Date: Jan. 21, 2010

(65) Prior Publication Data
US 2011/0123563 A1    May 26, 2011

(30) Foreign Application Priority Data
Jul. 18, 2008 (IT) .............................. VA2008A0043

(51) Int. Cl.
*C08B 37/00* (2006.01)
(52) U.S. Cl.
USPC .......................................... 536/114
(58) Field of Classification Search
None
See application file for complete search history.

(56) References Cited

U.S. PATENT DOCUMENTS 4,960,876 A * 10/1990 Molteni et al. ................. 536/114
5,256,651 A * 10/1993 Phelps et al. .................... 514/53

* cited by examiner

*Primary Examiner* — Layla Bland
(74) *Attorney, Agent, or Firm* — Mossman, Kumar & Tyler PC

(57) ABSTRACT

Cationic hydrophobically modified galactomannan ethers having a cationic degree of substitution ($DS_C$) from 0.01 to 0.5 and hydrophobic degree of substitution ($DS_H$) below 0.001 are readily soluble in aqueous systems and useful to thicken, stabilize and condition cosmetics, detergent compositions and household cleaning products; they further improve the deposition of other ingredients on the treated surface (skin, hair or fabric).

11 Claims, No Drawings

MODIFIED GALACTOMANNAN ETHERS

This invention relates to cationic hydrophobically modified galactomannan ethers having a cationic degree of substitution ($DS_C$) from 0.01 to 0.5 and hydrophobic degree of substitution ($DS_H$) below 0.001 suitable for the use in applications such as personal care and household care products.

The cationic hydrophobically modified galactomannan ethers of the present invention have the technologically useful property to be readily soluble in aqueous systems and to thicken, stabilize and condition cosmetic and detergent compositions.

Moreover the presence of a specific double substitution improves the deposition of other ingredients on the treated surface (skin, hair or fabric). A process for the preparation of these cationic hydrophobically modified galactomannan ethers is also described.

STATE OF THE ART

Galactomannans are polysaccharides composed mainly of galactose and mannose units.

The main source of galactomannans is the endosperm of certain leguminous seeds such as guar, carob, tara, *cassia obtusifolia* and the like. In particular, the polysaccharide contained in guar seeds consists of a main chain of mannose units linked together by 1-4-β-glycosidic linkages from which single galactose units branch by means of 1-6-α-glycosidic linkages.

The ratio of galactose units to mannose units can vary from one source to another. In the case of the polysaccharide contained in guar seeds the ratio is about 1:2.

Galactomannans are soluble in water to give high-viscosity solutions. For example the commercially available guar polysaccharide flower (guar gum) in a 1 weight % concentration in water gives a solution with a viscosity of between about 1,000 and about 9,000 mPa·s at 25 DEG C., when measured by a Brookfield RVT viscometer at 20 r.p.m. Galactomannan polysaccharides can also be derivatized, for example with hydroxyalkyl groups, to improve the basic performances of the polymer.

Their overall properties makes them particularly useful in various fields such as oil and gas drilling and production, paints and varnishes, textile printing, food and feed, paper, cosmetics and pharmaceutics.

Among the commercially available galactomannan derivatives used for modifying the rheological characteristics of aqueous systems it is difficult to find one which combines good viscosity-enhancing with adequate solubility properties, especially if dissolved electrolytes and surfactants are present.

In cosmetic products, moreover, there is a continuous search for new multifunctional products which possess these properties and enhanced conditioning and depositing power to a commercially useful extent. It is commonly acknowledged that cationic charges form a bond with the slightly anionic charges of various substrates, such as the keratin of hair and skin or the cellulose of the fabric.

A large series of cationic water-soluble polymers is used in cosmetic products and household cleaning products for their viscosity-enhancing, stabilizing and conditioning properties, especially in the preparation of shampoos, hair conditioners, creams, personal or household care detergents and softeners (see as an example Conditioning Agents for Hair & Skin, Ed. R. Schueller and P. Romanowski, Marcel Dekker Inc, NY, 1999). Cationic galactomannans, i.e. galactomannans bearing cationic substituents, and in particular, among these cationic derivatives of guar gum, have shown optimal results in improving the wet and dry combability of hairs washed with a shampoo formulated therewith. The cationic guar derivative generally used in cosmetic is known with the INCI name of Guar Hydroxypropyltrimonium Chloride and, chemically, is guar 2-hydroxy-3-(trimethylammonium)propyl ether chloride. In the patent literature cationic hydrophobically modified galactomannan ethers have generally been described as the reaction product of galactomannan with halo-alkyl or epoxy-alkyl trialkyl ammonium halide bearing at least one fatty alkyl chain, i.e. the hydrophobic portion and the cationic portion being introduced with a single etherifying agent.

For example, U.S. Pat. No. 5,202,048 describes personal cleansing compositions comprising surfactant and a cationic guar derivative in which at least one of the substituents on the nitrogen atom contains at least 2 and up to 24 carbon atoms and the degree of substitution is from about 0.5 to about 4. U.S. Pat. No. 5,473,059 discloses water soluble quaternary ammonium ethers of polysaccharides or polyols wherein one of the substituents on the nitrogen atom is an alkyl containing between about six and about 24 carbon atoms, the degree of substitution of said ethers ranging from about 0.001 to about 0.5.

U.S. Pat. No. 5,135,748 provides an aqueous composition which includes from about 0.01 to about 10% by weight of a cationic polysaccharide obtained through quaternization reaction with quaternary ammonium salts that may contain hydrophobes.

Recently published US 2008/0003192 (WO 2008/002666) reports in the examples some compositions comprising a cationic C4 "hydrophobically" modified guar; the C4 (butyl) degree of substitution of this modified guar is not disclosed; the stability of the compositions comprising the C4 modified guar is poor.

EP 189935 discloses hydrophobically modified cationic polysaccharides with $DS_H$ greater than 0; the polysaccharide may be a natural gum. However, EP 189935 does not explicitly mention the narrow $DS_H$ and $DS_C$ of the modified galactomannan ethers of the present invention. WO 01/85800 discloses in Example 7 a cationic guar that is enzimatically modified with a C36 alkyl ketene dimer; the $DS_H$ 0.015 of the purified resulting product may be calculated from its weight.

U.S. Pat. No. 5,256,651 discloses triple derivatives of polygalactomannan, in which the hydrophobic portion, the cationic portion and the hydroxyalkyl group are introduced separately, and the molecular substitution of the long aliphatic chain and of the dialkylaminoalkyl group are the same, from about 0.001 to about 0.2. The triple derivatives of U.S. Pat. No. 5,256,651 differs from the modified galactomannans of the present invention because the latter have $DS_H$ below 0.001.

The known cationic hydrophobically modified galactomannan ethers suffer from some disadvantages.

Short alkyl substituents, such as the $C_4$ alkyl chains of US 2008/0003192, leads to derivatives with poor stabilizing properties.

On the other hand, $C_{12}$-$C_{36}$ alkyl chains introduced through a cationic substituent provide water insoluble and poor dispersible products when acceptable conditioning property (i.e. effective cationic substitution) is requested; moreover, it is doubtful if such a bulky quaternary ammonium ion is still able to form a good bond with slightly anionic solid substrates. Furthermore, the prior art polygalactomannan, having high hydrophobic substitution, although ultimately water soluble, are poorly dispersible in water, tend to form lumps and their dissolution time is rather inadequate. Now it has now been found that cationic hydrophobically modified galactomannan ethers having $DS_H$ below 0.001 and obtained via a two steps reaction using a hydrophobizing etherifying agent and a cationizing etherifying agent are especially effective as stabilizers and conditioning agents for use in personal care and household cleaning products provided that they are synthesised with a selected specific cationic and hydrophobic degree of substitutions.

SUMMARY OF THE INVENTION

Cationic hydrophobically modified galactomannan ethers having a cationic degree of substitution ($DS_C$) from 0.01 to 0.5 and a hydrophobic degree of substitution ($DS_H$) from 0.00001 and below 0.001 are therefore the fundamental object of the present invention.

According to another aspect, the invention provides a process for preparing hydrophobically modified cationic galactomannan ethers having a cationic degree of substitution from 0.01 to 0.5 and hydrophobic degree of substitution from 0.00001 and below 0.001.

In a third aspect the invention provides cosmetic compositions and household cleaning products comprising from 0.1 to 10% by weight of the above defined galactomannan ethers.

DETAILED DESCRIPTION OF THE INVENTION

The cationic substituents of the galactomannan ethers derive from the reaction of part of the hydroxyl groups of the galactomannan with tertiary amino or quaternary ammonium alkylating agents, such as 2-dialkylaminoethyl chloride and quaternary ammonium compounds such as 3-chloro-2-hydroxypropyltrimethylammonium chloride, and 2,3-epoxypropyltrimethylammonium chloride. Examples include glycidyltrialkylammonium salts and 3-halo-2-hydroxypropyltrialkylammonium salts such as glycidyltrimethylammonium chloride, glycidyltriethylammonium chloride, gylcidyltripropylammonium chloride, glycidylethyldimethylammonium chloride, glycidyldiethylmethylammonium chloride, and their corresponding iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding iodides; and quaternary ammonium compounds such as halides of imidazoline ring containing compounds.

In the typical embodiments of the invention the cationizing alkylating agent contains quaternary ammonium groups and is (3-chloro-2-hydroxypropyl) trimethylammonium chloride.

The cationic substituent is in this case a 2-hydroxy-3-trimethylammoniumpropyl ether chloride group.

The tertiary amino or quaternary ammonium alkylating agents do not contain linear or branched alkyl chains having 4 or more carbon atoms.

The hydrophobic modification of the galactomannan ether of the invention is obtained by the introduction of hydrophobic substituents.

The useful hydrophobic substituents do not contain amine groups or quaternary ammonium groups and are chosen from the group consisting of linear or branched alkyl and/or alkenyl substituents of between 12 and 32 carbon atoms either alone or mixed together.

In the preferred embodiments of the invention the cationic substituent is 2-hydroxy-3-trimethylammoniumpropyl ether chloride and the hydrophobic substituent is a linear chain alkyl containing between 14 and 24 carbon atoms or a mixture of such alkyls.

The cationic hydrophobically modified galactomannan ether of the invention may further contain hydroxyethyl and/or 2-hydroxypropyl substituent groups, their total molar substitution degree ranging from 0.1 to 3, although galactomannan ethers containing only the cationic and the hydrophobic substituent are preferred.

In the present text, with the expression "cationic degree of substitution" ($DS_C$) we mean the molar cationic degree of substitution on the hydroxyl groups of guar measured by means of $^1$H-NMR; with the expression "hydrophobic degree of substitution" ($DS_H$) we mean the molar hydrophobic degree of substitution on the hydroxyl groups of guar measured by means of gas chromatography; the hydroxyethyl and/or hydroxypropyl molar substitution degree is also measured by means of $^1$H-NMR.

In the most preferred embodiments of the invention the cationic hydrophobically modified galactomannan ethers have $DS_{cat}$ from 0.1 to 0.3 and $DS_H$ between $5 \cdot 10^{-5}$ and $9 \cdot 10^{-4}$.

According to another embodiment, the hydrophobically modified cationic galactomannan ethers have $DS_C$ from 0.1 to 0.3, and $DS_H$ between $5 \cdot 10^{-5}$ and $9 \cdot 10^{-4}$, and hydroxypropyl molar substitution from 0.3 to 1.2.

The process for preparing the hydrophobically modified cationic galactomannan ethers of the present invention comprises the hydrophobic modification of a commercially available galactomannan gum, or hydroxyethyl and/or 2-hydroxypropyl galactomannan ether having a molar substitution from 0.1 to 3.0, and the reaction with tertiary amino or quaternary ammonium alkylating agents, preferably with 2,3-epoxypropyl trimethylammonium chloride or (3-chloro-2-hydroxypropyl) trimethylammonium chloride, in the presence of basic catalysts (such as sodium hydroxide).

When the cationic hydrophobically modified galactomannan ether also contains hydroxyethyl and/or 2-hydroxypropyl substituents, the hydroxyethyl and/or hydroxypropyl substituents may also be introduced in the last step, after hydrophobization and cationization of the galactomannan have occurred.

Therefore an alternative process for preparing hydrophobically modified cationic galactomannan ethers according to the present invention comprises the hydrophobic modification of a commercially available galactomannan gum, the reaction with tertiary amino or quaternary ammonium alkylating agents, preferably with 2,3-epoxypropyl trimethylammonium chloride or (3-chloro-2-hydroxypropyl) trimethylammonium chloride, and the reaction of the hydrophobically modified cationic intermediate with ethylene oxide and/or propylene oxide, in the presence of basic catalysts (such as sodium hydroxide), to give the cationic hydrophobically modified galactomannan ether containing hydroxyethyl and/or 2-hydroxypropyl substituents.

It has been found that the order in which the cationic and hydrophobic substituents are introduced on the guar backbone is relevant for the obtainment of the final product, being unexpectedly unfavourable to add hydrophobic substituents on cationic galactomanan ethers. Therefore, preferably, the reaction steps take place in the order given above, where the cationization follows the hydrophobic modification. The starting polysaccharides for obtaining the hydrophobically modified cationic modified galactomannan ether of the invention have a molecular weight typically of between 50,000 and 5,000,000 depending on the polysaccharide origin; preferably the polysaccharide is guar galactomannan.

Also, the cationic hydrophobically modified galactomannan ether of the invention has a molecular weight between 50,000 and 5,000,000. The reactants suitable for the hydrophobic modification include epoxy-alkanes and/or alkenes, alkyl- and/or alkenyl-glycidylethers, alkyl- and/or alkenyl-β-hydroxy-γ-chloropropyl ethers, and epoxy derivatives of triglycerides.

It is apparent that with the exception of the case in which the reactant is an alkyl and/or alkenyl halide, the hydrophobic substituent is not a simple alkyl and/or alkenyl radical. In effect, the substituent is a hydroxy-alkyl and/or alkenyl in the case of epoxy-alkanes and/or alkenes; a hydroxy-(oxa)-alkyl and/or alkenyl in the case of glycidyl ethers and β-hydroxy-γ-chloropropyl ethers. Notwithstanding this, the use of the term "alkyl and/or alkenyl substituents" was preferred in that, as regards the properties of the compounds of the present invention, substantial differences have not been noted between one compound and another, as far as they are chosen in the above list.

In a preferred embodiment of the process according to the invention the cationic hydrophobically modified galactomannan ether is obtained using guar gum as raw material and operating as follows: guar gum, possibly dispersed in an inert diluent in the form of lower aliphatic alcohols, ketones, or liquid hydrocarbons, is treated at ambient temperature with an alkaline hydroxide in aqueous solution and is then reacted with one of the said hydrophobizing reactants at a temperature of between 40° C. and 80° C. for a time of between 1 and 6 hours.

On termination of the reaction the system is set to 40° C. and the cationizing agent is introduced into the reactor, possibly dispersed in an inert organic diluent, and the reaction is completed by raising the temperature to 50-80° C. for 1-3 hours.

If the cationic hydrophobically modified galactomannan ether of the invention shall further contain hydroxyethyl and/or 2-hydroxypropyl substituents a third reaction step is required (hydroxyalkylating step). For use in cosmetic products and household cleaning compositions a purification step is usually required to obtain a particularly pure product. The purification step may take place by extraction of the impurities with an organic or aqueous-organic solvent before a final drying step so as to remove the salts and by-products formed during the reaction.

Or, advantageously, the purification step takes place by glyoxalation after termination of the synthetic steps (cationization, hydrophobization and hydroxyalkylation), as described for example in WO 2008/058768 or WO 03/078474.

The purified product obtained by means of glyoxalation is insoluble at pH lower than 7 and quickly and completely soluble at pH higher than 8; therefore it can be dispersed and dissolved readily in water.

The purification step may also take place by boron crosslinking of the starting galactomannan gum with sodium tetraborate decahydrate; at the end of the synthetic steps, the product having a pH higher than 9 is washed with water. The obtained purified product obtained can be dispersed in water, because of its insolubility at pH higher than 9, and quickly and completely dissolved at pH lower than 7.

As previously said, the cationic hydrophobically modified galactomannan ethers
having a cationic molar substitution from 0.01 to 0.5, and preferably from 0.1 to 0.3, a hydrophobic molar substitution from 0.00001 and below 0.001, and preferably from 0.00005 and 0.0009, in which the hydrophobic substituents do not contain amine groups or quaternary ammonium groups and are chosen from the group consisting of linear or branched alkyl and/or alkenyl substituents of between 12 and 32 carbon atoms either alone or mixed together are particularly useful as ingredients of cosmetic compositions and household cleaning products.

With the expression "cosmetic compositions" we mean the products normally used for personal care, such as hair care, skincare, sun care and oral care compositions.

Examples of cosmetic compositions are body, hands and face creams, hair gels and lotions (such as hair setting lotions, fixing and styling compositions, balms) hair colouring and bleaching creams, sunscreen compositions, make-up products (such as lipsticks, foundations, mascaras, eye-liners), cleansing, moisturizing and perspiring fluids, shampoos, perfumes, cleansing soaps and bars, toothpastes, mouthwashes, and other products for similar applications.

Household cleaning products include, but are not limited to: hard surface cleaning gels, bars, emulsions and liquid compositions, dry or damp dusting, cleaning and/or disinfecting wipes, fabric detergents and conditioners.

The galactomannan ethers of the present invention improve the deposition on hair and skin of the fatty ingredients of cosmetic compositions, such as oils, vitamines and emollients, and the persistence of their perfumes and fragrances, while providing effective conditioning and thickening effect.

They are easily dispersible and soluble in water, even in the presence of salts, and their thickening effect is not impaired by the presence of surfactants, which are normally present in cosmetic compositions and household cleaning products.

They are present in cosmetic compositions and household cleaning products in concentrations preferably ranging from 0.01 to 10% by weight relative to the total weight of the product, and more preferably from 0.05 and 2% by weight.

The cosmetic products of the invention contain the usual ingredients, such as surfactants, moisturizers, emollients, sunscreens, hydrophilic or lipophilic active agents such as ceramides, anti-free-radical agents, insect repellents, skin coolants, deodorants, antiperspirant actives, hair treatment agents, oral care agents, slimming agents, bactericides, sequestering agents, antidandruff agents, antioxidants, preserving agents, basifying or acidifying agents, fragrances, fillers, dyestuffs, other polymers and emulsifiers, gelling agents, foaming agents.

Also, the household cleaning products comprise the ingredients conventionally used in the fields, such as surfactants, emollients, insect repellents, bactericides, sequestering agents, antioxidants, preserving agents, basifying or acidifying agents, fragrances, fillers, dyestuffs, other polymers and emulsifiers, gelling agents, foaming agents, deodorizers, insecticides, cleaning agents, disinfectants, softeners, laundry detergents, dishwashing detergents.

The cosmetic and household cleaning products of the invention also contain an acceptable medium, which, according to the final use of the product, is usually compatible with any keratin substance, such as skin, nails, hair, wool and the like.

The acceptable medium may represent from 5% to 98% of the total weight of the product.

The typical acceptable medium is water.

Acceptable organic solvents may replace or partly substitute the water. The organic solvents may be hydrophilic organic solvents, lipophilic organic solvents, amphiphilic solvents or mixtures thereof.

Examples of hydrophilic organic solvents are linear or branched lower monoalcohols having from 1 to 8 carbon atoms, such as ethanol, propanol, butanol, isopropanol and isobutanol; polyethylene glycols having from 6 to 80 ethylene oxides; polyols such as propylene glycol, butylene glycol, glycerol and sorbitol; mono- or dialkyl isosorbide in which the alkyl groups have from 1 to 5 carbon atoms, such as dimethyl isosorbide; glycol ethers such as diethylene glycol monomethyl or monoethyl ether and propylene glycol ethers such as dipropylene glycol methyl ether.

Among the utilisable amphiphilic organic solvents we cite polyols such as polypropylene glycol (PPG) derivatives, such as fatty acid esters of polypropylene glycol and fatty alcohol ethers of PPG.

Utilisable lipophilic organic solvents are, for example, fatty esters such as diisopropyl adipate, dioctyl adipate and alkyl benzoates.

The cosmetic and household cleaning products of the present invention may be in the form of solution, emulsion, dispersion, gel, cream, paste, bar or wet wipe.

They may contain an oil, such as a mineral oil, a vegetable oil, an animal oil, a synthetic oil or mixture thereof.

Examples of utilisable oils are paraffins, liquid petroleum jelly, jojoba oil, coconut oil, sweet almond oil, olive oil, rapeseed oil, castor oil, sesame oil, avocado oil, groundnut oil, isoparaffins.

To better illustrate the invention, the following examples are reported to show the preparation of cationic galactomannans ethers according to the invention and the effect of their addition in exemplary cosmetic compositions.

Example 1

100 g of commercial guar flour, having Brookfield viscosity RVT at 20° C., 20 rpm and 1% by weight in water of 7000 mPa·s, is fed into a suitable steel reactor able to resist pressures up to 10 atm, evacuated and filled three times with nitrogen, and then mixed carefully with 0.3 g of sodiumtetraborate decahydrate and 8.8 g of sodium hydroxide in 47.5 g of a hydro-alcoholic solvent containing 53% by weight of isopropyl alcohol. After 30 minutes of stirring at 40° C., 0.5 g of hexadecylglycidylether (83% active content) dispersed in 12.5 g of hot isopropyl alcohol are added. The reactor is stirred until homogeneity and then heated to 70° C. for 1.5 hours. After this period, the reaction mixture is cooled to 40° C. and the pressure released, and 25.6 g of 3-chloro-2-hydroxypropyltrymethylammoniumchloride are added with 35.1 g of water and the reactor is heated up to 60° C. This temperature is kept for 1.5 hours under constant stirring. At the end of reaction, the alcohol is distilled, the mixture is cooled to 40° C. and the wet product obtained. Then 100 g of it are purified adding 830 g of ambient temperature water, mixed for 10 minutes, filtered off under vacuum. After drying in a hot air stream at 85-90 for 20 minutes, the product is ground and sieved through 100 mesh. The final polymer is a hydrophobically modified cationic guar having hexadecyl and cationic degree of substitution of $6.0 \cdot 10^{-4}$ and 0.15 respectively, and Brookfield viscosity RVT at 20° C., 20 rpm and 1% by weight in water of 5000 mPa·s.

Example 2

A cationic guar with a $C_{22}$ hydrophobic chain is obtained with the same procedure described in Example 1, starting from commercial guar flour, having Brookfield viscosity RVT at 20° C., 20 rpm and 1% by weight in water of 7000 mPa·s.

100 g of guar flour is added into a suitable steel reactor able to resist pressures up to 10 atm. The reactor is sealed, evacuated and filled three times with nitrogen. Then 0.3 g of sodiumtetraborate decahydrate and 8.8 g of sodium hydroxide in 47.5 g of a hydro-alcoholic solvent containing 53% by weight of isopropyl alcohol are added and carefully mixed. After stirring at 40° C. for 30 minutes, 0.5 g of $C_{22}$ alkyl glycidylether (85% active content) dispersed in 12.5 g of hot isopropyl alcohol are added and mixed until homogeneity. The reactor mass is heated to 70° C. and held at this temperature for 1.5 hours.

After this period, the reaction mixture is cooled to 40° C. and the pressure released. Then 25.6 g of 3-chloro-2-hydroxypropyltrymethylammoniumchloride are added with 35.1 g of water and the reactor is heated up to 60° C. After 1.5 hours under constant stirring, the alcohol is removed, the mixture is cooled to 40° C. and the wet product obtained. 100 g of it are purified adding 830 g of ambient temperature water, mixed for 10 minutes and filtered off under vacuum. After drying in a hot air stream at 85-90 for 20 minutes, the product is ground and sieved through 100 mesh.

The final polymer is a hydrophobically modified cationic guar having $C_{22}$ and cationic degree of substitution of $5.8 \cdot 10^{-4}$ and 0.14 respectively, and Brookfield viscosity RVT at 20° C., 20 rpm and 1% by weight in water of 5150 mPa·s.

Example 3

Cationic $C_{16}$ hydrophobically modified hydroxypropyl guar is obtained from the commercial guar flour used in Example 1 and 2, having Brookfield viscosity RVT at 20° C., 20 rpm and 1% by weight in water of 7000 mPa·s. To a suitable steel reactor able to resist pressures up to 10 atm, after three vacuum-nitrogen cycles to remove oxygen, 100 g of guar flour are added. Then 0.4 g of sodiumtetraborate decahydrate, dissolved in 25 g of sodium hydroxide 30% by weight aqueous solution, are added and carefully mixed. This mixture is stirred for 30 minutes at 40° C. Then 0.3 g of hexadecylglycidylether (83% active content), dispersed in 18.8 g of hot isopropyl alcohol, are added and mixed until homogeneity. The reactor mass is heated to 70° C. and held at this temperature for 1.5 hours. After this period, the reaction mixture is cooled to 40° C. and the pressure released. Then 23.1 g of 3-chloro-2-hydroxypropyltrymethylammoniumchloride are added with 25 g of water and the reactor is stirred for 15 minutes. Then 12.5 g of propylene oxide are added and the mixture is heated to 70° C. over a period of 30 minutes, then 22.5 g of propylene oxide are added in 30 minutes. This temperature is kept for 1.5 hours under constant stirring. Then the pressure is released and the alcohol removed, the mixture is cooled to 40° C. and the wet product obtained. 100 g of it are purified adding 830 g of ambient temperature water, mixed for 10 minutes and filtered off under vacuum. After drying in a hot air stream at 85-90 for 20 minutes, the product is ground and sieved through 100 mesh.

The final polymer is a hydrophobically modified cationic hydroxypropylguar having $C_{16}$ and cationic degree of substitution of $6.6 \cdot 10^{-5}$ and 0.12 respectively, hydroxypropyl molar substitution of 0.42 and Brookfield viscosity RVT at 20° C., 20 rpm and 1% by weight in water of 2150 mPa·s.

Example X

Comparative 100 g of commercial guar flour, having Brookfield viscosity RVT at 20° C., 20 rpm and 1% by weight in water of 7000 mPa·s, is fed into a suitable steel reactor able to resist pressures up to 10 atm, evacuated and filled three times with nitrogen, and then mixed carefully with 0.3 g of sodiumtetraborate decahydrate and 4.0 g of sodium hydroxide in 47.5 g of a hydro-alcoholic solvent containing 53% by weight of isopropyl alcohol. After 30 minutes of stirring at 40° C., 0.5 g of hexadecylglycidylether (83% active content) dispersed in 12.5 g of hot isopropyl alcohol are added. The reactor is stirred until homogeneity and then heated to 70° C. for 1.5 hours. After this period, the reaction mixture is cooled to 40° C. and the pressure released, and 1.0 g of 3-chloro-2-hydroxypropyltrymethylammoniumchloride are added with 35.1 g of water and the reactor is heated up to 60° C. This temperature is kept for 1.5 hours under constant stirring. At the end of reaction, the alcohol is distilled, the mixture is cooled to 40° C. and the wet product obtained. Then 100 g of it are purified adding 830 g of ambient temperature water, mixed for 10 minutes, filtered off under vacuum. After drying in a hot air stream at 85-90 for 20 minutes, the product is ground and sieved through 100 mesh. The final polymer is a hydrophobically modified cationic guar having hexadecyl and cationic degree of substitution of $5.5 \cdot 10^{-4}$ and 0.005 respectively, and Brookfield viscosity RVT at 20° C., 20 rpm and 1% by weight in water of 5200 mPa·s.

Example Y

Comparative

Cationic $C_{16}$ hydrophobically modified hydroxypropylguar is obtained from the commercial guar flour used in previous examples, having Brookfield viscosity RVT at 20° C., 20 rpm and 1% by weight in water of 7000 mPa·s.

To a suitable steel reactor able to resist pressures up to 10 atm, after three vacuum-nitrogen cycles to remove oxygen, 100 g of guar flour are added. Then 0.4 g of sodiumtetraborate decahydrate, dissolved in a mixture of 25 g of sodium hydroxide 30% by weight aqueous solution and 25 g of isopropyl alcohol, are added and carefully mixed. This mixture is stirred for 30 minutes at 40° C. Then 1.5 g of hexadecylglycidylether (83% active content), dispersed in 18.8 g of hot isopropyl alcohol, are added and mixed until homogeneity. The reactor mass is heated to 70° C. and held at this temperature for 1.5 hours. After this period, the reaction mixture is cooled to 40° C. and the pressure released. Then 23.1 g of 3-chloro-2-hydroxypropyltrymethylammoniumchloride are added with 25 g of water and the reactor is stirred for 15 minutes. Then 17.5 g of propylene oxide are added and the mixture is heated to 70° C. over a period of 30 minutes, then 21.3 g of propylene oxide are added in 30 minutes. This temperature is kept for 1.5 hours under constant stirring.

Then the pressure is released and the alcohol removed, the mixture is cooled to 40° C. and the wet product obtained. 100 g of it are purified adding 830 g of ambient temperature water, mixed for 10 minutes and filtered off under vacuum. After drying in a hot air stream at 85-90 for 20 minutes, the product is ground and sieved through 100 mesh.

The final polymer is a hydrophobically modified cationic hydroxypropylguar having $C_{16}$ and cationic degree of substitution of $3.0 \cdot 10^{-3}$ and 0.1 respectively, hydroxypropyl molar substitution of 1.1 and Brookfield viscosity RVT at 20° C., 20 rpm and 1% by weight in water of 750 mPa·s.

Application Examples

Example 4

Wet Detangling

Eight shampoos was prepared according to the formula reported in Table 1 and using conditioners reported in Table 2.

TABLE 1

| INCI name (or function) | Parts by weight |
|---|---|
| (Conditioner) | 0.5 |
| Sodium laureth sulfate (27% active matter) | 33 |
| Cocamidopropyl betaine (30% active matter) | 7 |
| Cocamide DEA (80% active matter) | 3 |
| Preservative | 0.2 |
| Citric acid (50% solution in water) | to pH 6 |
| Aqua | to 100 |

TABLE 2

| Shampoo No. | Conditioner | Chemical description |
|---|---|---|
| 1* | (Control) | Water |
| 2 | Example 1 | See Ex. 1 |
| 3 | Example 2 | See Ex. 2 |
| 4 | Example 3 | See Ex. 3 |
| 5* | Esaflor EC3 | Guar Hydroxypropyltrimonium Chloride |
| 6* | Esaflor HC56 | Hydroxypropyl Guar Hydroxypropyltrimonium Chloride |
| 7* | Ucare JR-30M | Polyquaternium-10 |
| 8* | Merquat 550 | Polyquaternium-7 |

*comparative

Each shampoo wash was carried out by applying about 4 g of each composition to 10 g of slightly bleached hair previously made wet (5 tresses of 2 g). The shampoo is worked into a lather and is then rinsed out thoroughly with water. The initiation of foaming is very easy and the foam is airy. Panelists are asked to disentangle tresses while time is measured. The average recorded times are given in Table 3.

TABLE 3

| Shampoo No. | Mean | Std dev |
|---|---|---|
| 1 | 48.0 | 7.5 |
| 2 | 40.7 | 7.0 |
| 3 | 35.5 | 4.1 |
| 4 | 32.6 | 3.7 |
| 5 | 33.6 | 7.7 |
| 6 | 34.5 | 3.4 |
| 7 | 41.3 | 5.6 |
| 8 | 52.1 | 6.4 |

Example 4bis

Comparative

Two more shampoos was prepared according to the formula reported in Table 1 and using the conditioners reported in Table 2b.

TABLE 2b

| Shampoo No. | Conditioner | Chemical description |
|---|---|---|
| X* | Example X* | See Ex. X |
| Y* | Example Y* | See Ex. Y |

*comparative

Each shampoo wash was carried out as in Example 4. Panelists are asked to disentangle tresses while time is measured. The average recorded times are given in Table 3b.

TABLE 3b

| Shampoo No. | Mean | Std dev |
|---|---|---|
| X* | 54.2 | 5.9 |
| Y* | 50.3 | 6.9 |

Example 5

Foaming Properties

Two Bath Foams (5A and 5B) were prepared according to the formulations of Table 4.

TABLE 4

| INCI NAME: | 5A (pbw) | 5B (pbw) |
|---|---|---|
| Aqua/Water | 10.00 | 10.00 |
| Guar Hydroxypropyltrimonium Chloride | — | 0.30 |
| Product of Example 1 | 0.30 | — |
| Lactic Acid | 0.05 | 0.05 |
| Sodium Laureth Sulfate | 45.00 | 45.00 |
| Sodium Cocoamphoacetate | 10.00 | 10.00 |
| Cocamide DEA | 3.00 | 3.00 |
| Phenoxyethanol | 0.60 | 0.60 |
| Diazolidynyl Urea | 0.30 | 0.30 |
| Lactic Acid | 0.90 | 0.90 |
| Panthenol | 0.20 | 0.20 |
| Silk Amino Acid | 1.00 | 1.00 |
| Fragrance | 1.00 | 1.00 |
| Aqua/Water | to 100 | to 100 |

Under continuous stirring, the product of Example 1 or the Guar Hydroxypropyltrimonium Chloride is first dispersed in water and neutralised with lactic acid. This solution, which contains about 1.5% of guar derivative, is then heated at 45° C. for 30 min to accelerate hydration. All other ingredients are added sequentially under moderate stirring to avoid foam formation.

The bath foams characteristics are reported in Table 5.

TABLE 5

| CHARACTERISTIC | 5B | 5A |
|---|---|---|
| Appearance | opaque | opaque |
| pH | 5.0-5.5 | 5.0-5.5 |
| Viscosity (RVT Brookfield, 5 rpm, 25° C.) | 24000 mPa·s | 30000 mPa·s |
| Foam draining time test | 80 sec | 40 sec |

The following foam draining test was used:
0.50 g of bath foam 5A or 5B are weighed on the technical balance in a 150 ml beaker. 50 ml of tap water are added, dissolved and transferred to the 1000 ml cup of a Waring Blender. With other 50 ml of water the beaker is rinsed and the water is transferred in the cup.

The solution is stirred for 60 second at high speed. At the end of the agitation immediately all the content of the cup is poured in a 1000 mL cylinder. The time in which 50 mL of liquid separate from the foam is recorded.

The foam obtained using the product of Example 1 is more rich and persistent.

Example 5b

Comparative

A Bath Foam (5C) was prepared according to the formulations of Table 4b and the same procedure of Example 5.

TABLE 4b

| INCI NAME: | 5C (pbw) |
|---|---|
| Aqua/Water | 10.00 |
| Product of Example Y | 0.30 |
| Lactic Acid | 0.05 |
| Sodium Laureth Sulfate | 45.00 |
| Sodium Cocoamphoacetate | 10.00 |
| Cocamide DEA | 3.00 |
| Phenoxyethanol | 0.60 |
| Diazolidynyl Urea | 0.30 |
| Lactic Acid | 0.90 |
| Panthenol | 0.20 |
| Silk Amino Acid | 1.00 |
| Fragrance | 1.00 |
| Aqua/Water | to 100 |

The bath foam characteristics (evaluated as in Example 5) are reported in Table 5b.

TABLE 5b

| CHARACTERISTIC | 5C |
|---|---|
| Appearance | Very opaque |
| pH | 5.0-5.5 |
| Viscosity (RVT Brookfield, 5 rpm, 25° C.) | 15000 mPa·s |
| Foam draining time test | 35 sec |

Example 6

Emulsifying properties. Six emulsions were prepared by stirring 50 ml of Squalane, Octyl Palmitate and Sunflower Oil with 200 ml of water in presence of 1% of respectively Guar Hydroxypropyltrimonium Chloride and the product of Example 2. After vigorous mixing the emulsions were put in a centrifuge tube and centrifuged at 6000 rpm. After 30 min all the emulsions prepared using Guar Hydroxypropyltrimonium Chloride were completely separated while the emulsions prepared using the product of Example 2 were still well emulsified.

Example 7

Alpha-Hydroxy Acids Emulsifier Free Skin Cream

An alpha-hydroxy acids emulsifier free skin cream was prepared with the ingredients reported in Table 6 and the following procedure.

TABLE 6

| PHASE | INCI NAME | % |
|---|---|---|
| | A | |
| 1 | Sodium Polyacryloyldimethyl Taurate (and) Hydrogenated Polydecene (and) Trideceth-10 | 4.00 |
| 2 | Mineral Oil | 15.00 |
| 3 | Sunflower Oil | 6.00 |
| 4 | Jojoba Oil | 4.00 |
| 5 | BHT | 0.05 |
| | B | |
| 1 | Aqua/Water | to 100 |
| 2 | Guar Hydroxypropyltrimonium Chloride or product of Example 2 | 0.60 |
| 3 | Sodium Lactate (60% active matter) | 15.00 |
| 4 | Citric Acid (50% solution in water) | to pH 4-4.5 |

TABLE 6-continued

| PHASE | INCI NAME | % |
|---|---|---|
| C | | |
| 1 | Fragrance | QS |
| D | | |
| 1 | Preservatives | QS |

Procedure:

Mix ingredients of phase A.

Put water into a vessel, then add Sodium Lactate. Disperse the guar derivative into the batch and add Citric Acid.

Heat to 60° C. phase A and phase B.

Emulsify A into B.

Let the batch cool down while homogenizing.

When T=30° C. add phase C and phase D.

Continue homogenising until a smooth cream is obtained.

The characteristics of the cream are the following:
Appearance: white emulsion
pH: 3.5-3.8
Viscosity (RVT Brookfield®, 5 rpm, 25° C.): approx 50.000 mPa·s The cream prepared using Guar Hydroxypropyltrimonium Chloride do not pass stability test at 40° C. (3 months emulsion stability test). The cream prepared using the guar derivative of Example 2 is an emulsion which is stable for more than 3 month at 40° C.

Example 7

Fabric Detergent

To 1000 ml Dash regular liquid detergent (commercial product), 100 ml of a 2% solution of Guar Hydroxypropyltrimonium Chloride or product of Example 1 were added and mixed well.

Fabric Treatment 3 fabric treatments (one-reference blank treatment and 2 treatments with the products to be tested) are made in parallel on 3 washing machines at the same time.

Washing Conditions:
Machines: Miele W934
Load: 5 pillow cases and 4 little terry towels (30×50 cm)=1 kg
Water hardness: 0° F.
Temperature: 40° C.
Spin rate: 600 RPM
Program: short program (1 h 16)

All fabrics from different treatment are line-dried at the same time at room temperature (temperature and relative humidity controlled).

Panel Test

The following questions are asked to 16 panelists. One terry towel is used for 4 panelists and after is replaced by another one.

"Which towel is the most perfumed?"
"Which towel is the less perfumed?"

Results 13 people reported that the towel washed with the detergent containing the product of Example 1 (dosed at 0.2% wt in the detergent composition) increased significantly the perfume effect into the Dash liquid detergent.

The invention claimed is:

1. Cationic hydrophobically modified galactomannan ethers having cationic degree of substitution (DSc) from 0.01 to 0.5 and hydrophobic degree of substitution ($DS_H$) from 0.00001 and below 0.001, in which the hydrophobic substituents are chosen from the group consisting of linear or branched alkyl and/or alkenyl substituents having between 12 and 32 carbon atoms.

2. Cationic hydrophobically modified galactomannan ethers according to claim 1 whose cationic substituents are 2-hydroxy-3-[trimethylammonium]propyl ether chloride groups.

3. Cationic hydrophobically modified galactomannan ether according to claim 2 containing only cationic and hydrophobic substituents.

4. Cationic hydrophobically modified galactomannan ether according to claim 2 further containing hydroxyethyl and/or 2-hydroxypropyl groups.

5. Cationic hydrophobically modified galactomannan ether according to claim 4 in which the total molar substitution of hydroxyethyl and/or hydroypropyl groups ranges from 0.1 to 3.

6. Cationic hydrophobically modified galactomannan ethers according to claim 1 having DSc from 0.1 to 0.3 and $DS_H$ between $5·10^{-5}$ and $9·10^{-4}$.

7. Cationic hydrophobically modified galactomannan ethers according to claim 5 having DSc from 0.1 to 0.3, $DS_H$ between 0.00005 and 0.0009, and hydroxypropyl molar substitution from 0.3 to 1.2.

8. Cosmetic compositions containing from 0.01 to 10% by weight of a cationic hydrophobically modified galactomannan ether according to claim 1.

9. Cosmetic compositions according to claim 8 containing one or more ingredient selected from surfactants, moisturizers, emollients, sunscreens, hydrophilic or lipophilic active agents such as ceramides, anti-free-radical agents, insect repellents, skin coolants, deodorants, antiperspirant actives, hair treatment agents, oral core agents, slimming agents, bactericides, sequestering agents, antidandruff agents, antioxidants, preserving agents, basifying or acidifying agents, fragrances, fillers, dyestuffs, other polymers and emulsifiers, gelling agents, foaming agents.

10. Household cleaning products containing from 0.01 to 10% by weight of a cationic hydrophobically modified galactomannan ether according to claim 1.

11. Household cleaning products according to claim 10 containing one or more ingredient selected from surfactants, emollients, insect repellents, bactericides, sequestering agents, antioxidants, preserving agents, basifying or acidifying agents, fragrances, fillers, dyestuffs, other polymers and emulsifiers, gelling agents, foaming agents, deodorizers, insecticides, cleaning agents, disinfectants, softeners, laundry detergents, dishwashing detergents.

* * * * *